(12) United States Patent
Hayakawa et al.

(10) Patent No.: US 8,029,821 B2
(45) Date of Patent: Oct. 4, 2011

(54) CAPSULE COMPRISING LOW-SUBSTITUTED CELLULOSE ETHER AND METHOD FOR PREPARING THE SAME

(75) Inventors: Kazuhisa Hayakawa, Niigata-ken (JP); Naosuke Maruyama, Niigata-ken (JP); Miyuki Fukasawa, Niigata-ken (JP)

(73) Assignee: Shin-Etsu Chemical Co. Ltd. (JP)

( * ) Notice: Subject to any disclaimer, the term of this patent is extended or adjusted under 35 U.S.C. 154(b) by 586 days.

(21) Appl. No.: 11/018,594

(22) Filed: Dec. 20, 2004

(65) Prior Publication Data

US 2005/0142186 A1 Jun. 30, 2005

(30) Foreign Application Priority Data

Dec. 25, 2003 (JP) ................................ 2003-429276

(51) Int. Cl.
 *A61K 9/48* (2006.01)
 *A61K 9/62* (2006.01)
(52) U.S. Cl. ........................................ 424/451; 424/461
(58) Field of Classification Search ........................ None
 See application file for complete search history.

(56) References Cited

U.S. PATENT DOCUMENTS

| | | | |
|---|---|---|---|
| 4,091,205 A | 5/1978 | Onda et al. | |
| 4,948,622 A * | 8/1990 | Kokubo et al. | 427/2.16 |
| 4,993,137 A | 2/1991 | Muto et al. | |
| 5,032,074 A | 7/1991 | Muto et al. | |
| 5,464,612 A * | 11/1995 | Matoba et al. | 424/78.1 |
| 6,280,767 B1 * | 8/2001 | Sano et al. | 424/456 |
| 6,306,333 B1 | 10/2001 | Rosenberg et al. | |
| 7,262,181 B2 * | 8/2007 | Zhang et al. | 514/57 |
| 2003/0166611 A1 * | 9/2003 | Obara | 514/57 |

FOREIGN PATENT DOCUMENTS

| | | |
|---|---|---|
| EP | 1 045 000 A1 | 10/2000 |
| EP | 1045000 A1 * | 10/2000 |
| EP | 1 342 733 A1 | 9/2003 |
| GB | 643853 | 1/1947 |
| JP | 54-105223 | 8/1979 |
| JP | 55-137102 | 10/1980 |
| JP | 57-53100 | 11/1982 |
| JP | 60-66935 | 4/1985 |
| JP | 60-102138 | 6/1985 |
| JP | 61-281182 | 12/1986 |
| JP | 2-203741 | 8/1990 |
| JP | 5-65222 | 3/1993 |
| WO | WO 02/060384 A2 | 8/2002 |
| WO | WO 0287643 A1 * | 11/2002 |

OTHER PUBLICATIONS

European Search Report from corresponding European Application No. 04258045.6-1219, search report dated Apr. 28, 2005, communication dated Jun. 15, 2005.
Japanese Office Action from corresponding Japanese Application No. 2003-429276, mailed Oct. 20, 2009.

\* cited by examiner

*Primary Examiner* — Susan Tran
(74) *Attorney, Agent, or Firm* — Alston & Bird LLP

(57) ABSTRACT

A capsule with good disintegration properties that can quickly display its content's efficacy as well as a method for preparing the same are provided. More specifically, provided is a capsule comprising a shell comprising low-substituted cellulose ether. Also, provided is a method for preparing a hard capsule comprising the low-substituted cellulose ether comprising a step of covering a pin for forming the hard capsule with the low-substituted cellulose ether by immersing the pin in an alkaline solution of the low-substituted cellulose ether; a step of forming the low-substituted cellulose on a surface of the pin into a gel by further immersing the covered pin in an aqueous acid solution; a step of washing by immersing the pin whose surface has been covered with the gel in water; and a step of drying.

12 Claims, No Drawings

CAPSULE COMPRISING LOW-SUBSTITUTED CELLULOSE ETHER AND METHOD FOR PREPARING THE SAME

BACKGROUND OF THE INVENTION

1. Field of the Invention

The present invention relates to a capsule with improved disintegration comprising low-substituted cellulose ether that is mainly used for food and pharmaceutical products and to a method for preparing the same.

2. Description of the Related Art

Generally, a shell of a hard or soft capsule comprises a water-soluble shell-forming component such as gelatin, agar, carrageenan, hydroxypropylmethylcellulose and the like. And a hard capsule is prepared, for example, by filling a content into a hard capsule shell formed by adhering an aqueous solution of gelatin onto a mold pin and drying the solution.

On the other hand, a soft capsule is prepared, for example, by encapsulating a content by a soft capsule shell that are obtained by forming a gel from a shell base substrate comprising gelatin, water and a plasticizer.

However, the conventional shell for the capsule described above has the following problems:

(1) Because eicosapentanoic acid (hereafter referred to as "EPA"), docosahexaenoic acid (hereafter referred to as "DHA"), 3-carotene or the like, which is believed to be generally effective for the prevention of lifestyle diseases and the like, has many double bonds within the molecule, it is very easily oxidizable substance. Furthermore, because the substance has unpleasant taste and odor, it cannot be generally admixed to food as it is. Consequently, the substance is ordinarily used as health food sealed in a soft capsule. A method of adding the substance to food after sealing in a soft capsule is widely known (Japanese Patent Application Unexamined Publication No. 60-102138/1985, Japanese Patent Application Unexamined Publication No. 60-66935/1985, and Japanese Patent Application Unexamined Publication Nos. 2-203741/1990 and 5-65222/1993). However, although the methods can veil the unpleasant taste and odor, an oxidation of content cannot be completely prevented, so that the peroxide value increases as time passes, and the content turns yellow.

(2) Because the capsule used in pharmaceutical products or health food is generally required to have good intragastric dissolution after intake and the content's efficacy is displayed quickly, the improvement of the dissolution of a capsule has been an important problem to be solved. But nevertheless, water-soluble polymers that are soluble in water but do not disintegrate and tend to form a thick gel film are presently used for the capsule base substrate.

SUMMARY OF THE INVENTION

In view of the above problems, it is an object of the present invention to provide a capsule that has good disintegration properties and that can quickly display its content's efficacy as well as a method for preparing the same.

As a result of intensive studies to attain this object, the inventors have focused on the various properties of low-substituted cellulose ether that does not dissolve but swells in water, and dissolves in an alkaline aqueous solution, and completed the present invention by finding that favorable disintegration properties are achieved and the content's efficacy can be quickly displayed and the drug does not undergo denaturation when using low-substituted cellulose ether as a base substrate for the capsule.

Therefore, the present invention provides a capsule comprising the following low-substituted cellulose ether and a method for preparing the same.

According to the present invention, provided is a capsule comprising a shell comprising low-substituted cellulose ether.

Moreover, according to the present invention, provided is a method for preparing a hard capsule comprising a low-substituted cellulose ether comprising a step of covering a pin for forming the hard capsule with the low-substituted cellulose ether by immersing the pin in an aqueous alkaline solution of the low-substituted cellulose ether; a step of forming the low-substituted cellulose on the surface of the pin into a gel by further immersing the covered pin in an aqueous acid solution; a step of washing by immersing in water the pin whose surface has been covered with the gel; and a step of drying.

According to the present invention, provided is a method for preparing a soft capsule comprising a low-substituted cellulose ether comprising a step of casting an aqueous alkaline solution of the low-substituted cellulose ether to obtain a sheet; a step of forming a gel sheet of the low-substituted cellulose by immersing the obtained sheet in an aqueous acid solution; a step of washing by immersing the gel sheet in water; a step of drying; and a step of molding by introducing the dried gel sheet into a film-introducing part of a gelatin soft capsule molding apparatus.

Furthermore, according to the present invention, provided is another method for preparing a hard capsule comprising a low-substituted cellulose ether comprising a step of preparing an aqueous solution by dispersing the low-substituted cellulose ether in water and further dispersing it by a shearing force; a step of covering a pin for forming the hard capsule with the low-substituted cellulose ether by immersing the pin in this dispersion; and a step of drying.

Furthermore, according to a present invention, provided is another method for preparing a soft capsule comprising low-substituted cellulose ether comprising a step of preparing a dispersion by dispersing the low-substituted cellulose ether in water; a step of applying a shearing force to the dispersion; a step of forming a sheet by casting the dispersion to which the shearing force have been applied; a step of drying the obtained sheet; and a step of molding by introducing the dried sheet into a film-introducing part of the gelatin soft capsule molding apparatus.

The capsules comprising the low-substituted cellulose ether of the present invention are useful because their disintegration is good, the content's efficacy can be quickly displayed, and the drug hardly undergoes deterioration.

DETAILED DESCRIPTION OF THE PREFERRED EMBODIMENTS

According to the present invention, low-substituted cellulose ether has properties that it is insoluble in water, but swells by absorbing water, and is soluble in an aqueous alkaline solution. A typical example may include low-substituted hydroxypropylcellulose, which is currently commercially available under the trade name "L-HPC" by Shin-Etsu Chemical Co., Ltd. The low-substituted cellulose ether is listed in Japanese Pharmacopoeia and is widely used as a disintegrating agent that is formulated in a tablet especially in the field of pharmaceutical materials.

Cellulose is generally insoluble in water, but if a hydrogen atom of the hydroxyl group of the glucose ring constituting the cellulose is substituted with an alkyl group or a hydroxyalkyl group, then the cellulose becomes soluble in water depending on the degree of substitution. However, in many cases, cellulose in which the degree of substitution is low does not dissolve in water, swells, and dissolves in an aqueous alkaline solution. In most cases, when a powder of low-substituted cellulose ether is dispersed in water, a part of the cellulose ether swells.

If the substitution degree is high, then cellulose ether becomes soluble in water but conversely loses the solubility in an alkaline solution. Therefore, if such water soluble cellulose ether is used, then it is impossible to obtain a gel of the present invention.

The cellulose ether used in the present invention may be cellulose ether having the substitution degree of 0.05 to 1.0 for the low substitution or cellulose ether having the substitution degree of 0.1 to 0.8 for solubility in an aqueous alkaline solution. More specific examples are the low-substituted cellulose ethers described below:

Low-substituted methylcellulose having a substitution degree of 0.16 to 0.84 for a methoxyl group; low-substituted hydroxyethylcellulose having a substitution degree of 0.1 to 0.5 for a hydroxyethoxyl group; low-substituted hydroxypropylcellulose having a substitution degree of 0.1 to 0.5 for a hydroxypropoxyl group; low-substituted hydroxypropylmethylcellulose having a substitution degree of 0.1 to 0.5 for a methoxyl group and a substitution degree of 0.1 to 0.5 for a hydroxypropoxyl group; and low-substituted carboxylmethylcellulose and a sodium salt thereof having a substitution degree of 0.1 to 0.8 for a carboxymethyl group.

The substitution degree of low-substituted cellulose ether can be determined by the method mentioned in Japanese Pharmacopoeia.

A method for preparing low-substituted cellulose ether are widely known in the art and disclosed in Japanese Patent Examined Application No. 57-53100/1982, for example. That is, alkali cellulose can be prepared by immersing a pulp sheet serving as a starting material in an aqueous alkaline solution such as sodium hydroxide, or by mixing pulverized pulp in an aqueous alkaline solution, or by adding a base to a dispersion of pulp powder in an organic solvent, or by the other method.

Next, the alkali cellulose may be placed in a reactor. Following the addition of an etherification agent such as propylene oxide, ethylene oxide or the like, the alkali cellulose may be heated to react so as to obtain cellulose ether.

After the reaction, the crude cellulose ether may be transferred to another tank where the alkali is neutralized with acid so as to obtain a solid material. The solid material is washed, dried, and pulverized into powder as a final product.

Alternatively, the crude cellulose ether may be completely or partially dissolved in water immediately after the reaction and then be neutralized, and the precipitated cellulose polymer may be collected and then washed, dried, and pulverized.

Examples of the base used for the alkali solution may include potassium hydroxide, sodium hydroxide or the like. The concentration of the base is determined appropriately, depending on the kind and substitution degree of substituent of the cellulose ether used. The typical concentration may be preferably 2 to 25% by weight, more preferably 3 to 15% by weight. In a typical example, low-substituted hydroxypropylcellulose having a substitution degree of 0.2 may be dissolved in 10% by weight of NaOH.

It should be noted that there are cases in which the solution is transparent and cases in which it is not completely transparent, due to the difference in the distribution of the substituent group. In the latter case, the cellulose ether is considered to be dissolved when the viscosity of the solution has clearly risen.

Examples of the acid to be used may include hydrochloric acid, sulfuric acid, acetic acid and the like and it may be preferable that the concentration corresponds to an amount that can stoichiometrically neutralize the concentration of the aqueous alkaline solution used.

In general, two methods described below can be given as examples of the methods for preparing a capsule comprising low-substituted cellulose ether of the present invention using the low-substituted cellulose ether described above.

In a first method, a pin for forming a hard capsule is immersed in an aqueous alkaline solution in which the low-substituted cellulose ether is dissolved, then the pin is lifted up and then immersed in an aqueous acid solution to cover the pin with a gel film of the low-substituted cellulose ether which contains the salt generated in the reaction of the aqueous acid solution and the aqueous alkaline solution. The pin covered with the gel film are then immersed in water for washing and later dried, thus obtaining a hard capsule-forming body.

It may be preferable that the concentration of the aqueous alkaline solution of the low-substituted cellulose ether is such that the solution is viscous enough that dripping of the solution is reduced to a minimum when the pin is drawn up from the solution. The concentration of 10 to 30% by weight may be particularly preferable. There is no particular limitation regarding the pin for forming the hard capsule and any pin as known in the art can be used. By immersion in the aqueous acid solution, the aqueous alkaline solution contained by the low-substituted cellulose ether which is present on the surface of the pin is neutralized. A gel film of the low-substituted cellulose ether is formed and the pin is covered with the gel film. At this time, the salt formed by the neutralization is present in the gel film, but the salt will be removed by washing in the subsequent step. There is no particular limitation regarding the drying and any of the drying methods known in the art can be used. The thickness of the capsule containing the low-substituted cellulose ether can be adjusted by the concentration of the aqueous alkaline solution of the low-substituted cellulose ether or the like, but the thickness may be preferably 10 to 50 μm.

In a method for preparing a soft capsule, the aqueous alkaline solution of the low-substituted cellulose ether may be cast on a substrate, then the cast portion is immersed in an aqueous acid solution, and while still containing the resulting salt, the gel sheet of low-substituted cellulose is formed. After immersing the gel film sheet in water for washing, it is washed and dried. The obtained gel sheet can be molded by introducing the gel sheet preferably into a film-introducing part of a gelatin capsule molding apparatus.

In this method for preparing a soft capsule, the concentration of the low-substituted cellulose ether in the aqueous alkaline solution may depend on the ease of the casting. It may be preferable that the concentration is 10 to 30% by weight. The casting may be performed by applying the low-substituted cellulose ether on a known substrate of glass or synthetic resin such as polyethylene terephthalate, polypropylene or the like, and adjusting the thickness of the applied low-substituted cellulose ether with a doctor blade, thus obtaining a sheet of the low-substituted cellulose ether. The gel sheet is a sheet in which the surface of the low-substituted cellulose ether sheet has been formed into a gel. There is no particular limitation to the gelatin capsule molding apparatus and any apparatus known in the art can be used, such as the rotary soft capsule R&D model SSC-A3 by Sankyo Co., Ltd., for example. The thickness of the sheet before the introduction into the gelatin capsule forming apparatus may be preferably 0.05 to 0.20 μm, and the thickness of the sheet obtained after the molding with the gelatin capsule-forming apparatus may be preferably 0.03 to 0.15 mm.

After washing, the gel pin or the gel sheet may be immersed in a plasticizer solution containing glycerin, propylene glycol, ethylene glycol or their derivative or an aqueous solution containing the same, and may be impregnated with the plasticizer. With subsequent drying, it may be possible to obtain even a softer hard capsule or soft capsule. Instead of the plasticizer solution, it may be also possible to add an appropriate amount of starch, pullulan or chitin in order to adjust the disintegrating properties. The amount of plasticizer may be preferably 10 to 30% by weight and the concentration of the plasticizer solution may be preferably 10 to 50% by weight.

Another method for preparing the capsule comprising the low-substituted cellulose ether may comprise steps of dispersing the low-substituted cellulose ether in water, applying a shearing force to the dispersion, immersing a pin in the cellulose ether dispersion which has been subjected to the shearing force, washing and drying so as to obtain a hard capsule forming body.

The dispersion of the low-substituted cellulose ether can be prepared by using preferably 2 to 10 parts by weight of low-substituted cellulose ether in 100 parts by weight of water. Application of the shearing force may be performed by collision of the low-substituted cellulose ether against each other, collision of the cellulose ether against a collision board, shear-triturating, for example. However, there is no limitation to this, and as long as being dispersed by wet pulverization is done, any method can be applied. There is no particular limitation to the pin, and a pin similar to the pin described above may be used. The surface of the pin may be covered by immersing it in this dispersion. Drying may performed by any known method. The thickness of the capsule comprising the low-substituted cellulose ether can be adjusted preferably in the range of 0.03 to 0.2 mm, more preferably in the range of 0.05 to 0.15 mm.

Another method for preparing a soft capsule can comprise steps of forming a cellulose ether dispersion, which has been obtained by applying a shearing force similarly as described above, into a sheet by casting or the like; drying; and introducing the sheet preferably into the film-introducing part of a gelatin capsule molding apparatus so as to form the soft capsule, for example. The casting and the gelatin capsule molding apparatus may be the same as described above.

In order to provide the capsule shell with softness, the plasticizer solution containing glycerin, propylene glycol, ethylene glycol or their derivative, or an aqueous solution containing the same can be added to the dispersion which has been subjected to shear-triturating. The resulting mixture can be used in the same manner so as to form soft as well as hard capsules. Furthermore, at this point, starch, pullulan or chitin instead of the plasticizer solution can be added in an appropriate amount in order to adjust the disintegration properties.

There is no particular limitation regarding the apparatus for preparing the cellulose ether dispersion obtained by collision of the low-substituted cellulose ether with each other, by collision of the low-substituted cellulose ether against a collision board, or by shear-triturating. Examples of the suitable apparatus may include vibration ball mills, colloid mills such as the Masscolloider or the Cerendipitor by Masuko Sangyo Co., Ltd., homomixers and propeller-type homogenizers. The homogenizers may preferably include the homogenizer by Sanwa Machine Co., Inc., which subjects the low-substituted cellulose ether to collisional friction by discharging a treating liquid from a slit of a valve with high pressure; the Ultimaizer System by Sugino Machine Limited; the Microfluidizer by Mizuho Industrial Co., Ltd.; the Gaulin high-pressure homogenizer; and an ultrasonic homogenizer that utilizes vibration of ultrasonic waves such as the ultrasonic homogenizer by Nippon Seiki Co., Ltd. These homogenizers are preferably used for preparing homogeneous dispersions. Furthermore, it is also possible to use dispersions that have been repeatedly treated by these apparatuses.

The present invention is explained in detail below through examples as well as comparative examples, but the present invention is not construed as limited to the embodiments below.

Example 1 and Comparative Example 1

The 10 g of low-substituted hydroxypropylcellulose powder (L-HPC by Shin-Etsu Chemical Co., Ltd; a substitution degree of 0.2) was dissolved in 90 g of an aqueous 10% by weight NaOH solution.

A male pin and a female pin for capsule formation with an internal diameter of 5 mm were immersed in the NaOH solution, and then immersed in an aqueous 10% by weight hydrochloric acid solution, resulting in a state in which a gel film of low-substituted hydroxypropylcellulose containing the salt covers the pins. After the pins with the gel film were immersed in water and washed, the pins were then dried at 30° C. to obtain a hard capsule containing vitamin C. Gelatin capsules were also prepared by a conventional method. The capsules were subjected to a disintegration test according to Japanese Pharmacopoeia on six capsules each.

The soft capsules comprising L-HPC disintegrated within 1 minute, while the gelatin capsules disintegrated in the range of 3 to 5 minutes.

Also, observing the yellowing change of the vitamin C in the capsules stored at 40° C. for one month, there was clearly less yellowing in the capsules of the present invention than in the gelatin capsules.

Example 2 and Comparative Example 2

The 10 g of low-substituted hydroxypropylcellulose powder (L-HPC by Shin-Etsu Chemical Co., Ltd; a substitution degree of 0.2) was dissolved in 90 g of an aqueous 10% by weight NaOH solution.

The solution was cast on a polyethylene terephthalate sheet (width: 400 mm width, length: 600 mm length and thickness: 50 μm) on a table coater by Hirano Tecseed Co., Ltd. The sheet was coated with a blade to a thickness of 15 mm. Then, the cast portion along with the sheet of polyethylene terephthalate was immersed for 2 minutes in a vat holding a 12% by weight hydrochloric acid solution, washed by immersion for 3 minutes in a vat holding tap water, and then immersed in an aqueous 10% by weight glycerin solution for 1 minute. Then, the cast portion was dried for 24 hours at 20° C. to produce a dried sheet having thickness of about 150 μm. The Oval-5 soft capsules containing refined sardine oil were prepared by stamping the sheet in use of a rotary die. Soft capsules comprising gelatin were also prepared in the same method. The capsules were subjected to the disintegration test according to Japanese Pharmacopoeia on six capsules each.

The soft capsules comprising L-HPC disintegrated within 1 minute, while the gelatin capsules disintegrated in the range of 3 to 5 minutes.

Example 3 and Comparative Example 3

The 100 g of low-substituted hydroxypropylcellulose powder (L-HPC by Shin-Etsu Chemical Co., Ltd; a substitution degree of 0.2) was dispersed in 900 g of water and treated 10 times with a Cerendipitor by Masuko Sangyo Co., Ltd. to obtain the dispersion. After a male pin and a female pin for capsule formation having an internal diameter of 5 mm were immersed in the dispersion, lifted up and dried at 30° C. to obtain a hard capsule forming body containing vitamin C inside. Gelatin capsules were also prepared in a conventional method. The capsules were subjected to the disintegration test according to Japanese Pharmacopoeia on six capsules each.

The soft capsules comprising L-HPC disintegrated within 1 minute, while the gelatin capsules disintegrated in the range of 3 to 5 minutes.

Also, observing the yellowing change of the vitamin C in the capsules stored at 40° C. for one month, there was clearly less yellowing in the capsules of the present invention than in the gelatin capsules.

Example 4 and Comparative Example 4

After 100 g of low-substituted hydroxypropylcellulose powder (L-HPC by Shin-Etsu Chemical Co., Ltd; a substitution degree of 0.2) was dispersed in 900 g of water, this dispersion was treated 10 times by the Microfluidizer 110-EH by Mizuho Industrial Co., Ltd., at a pressure of 172 MP. The resulting dispersion was cast on a polyethylene terephthalate sheet (width: 400 mm width, length: 600 mm length, thickness: 50 μm) with the table coater by Hirano Tecseed Co., Ltd. The sheet was coated with a blade to a thickness of 15 mm. The sheet was then dried for 24 hours at 20° C. so as to produce a dried sheet having thickness of about 150 μm. The Oval-5 type soft capsules containing refined sardine oil were prepared by stamping the sheet with a rotary die machine. Soft capsules comprising gelatin were also prepared in the same manner. The capsules were subjected to the disintegration test according to Japanese Pharmacopoeia on six capsules each.

The soft capsules comprising L-HPC disintegrated within 1 minute while the gelatin capsules disintegrated in the range of from 3 to 5 minutes.

What is claimed is:

1. A capsule comprising a shell consisting of low-substituted cellulose ether having a substitution degree of 0.1 to 0.8 which is insoluble in water but soluble in an aqueous alkaline solution, wherein said capsule is a hard capsule into which an active ingredient is filled.

2. A capsule according to claim 1, wherein the low-substituted cellulose ether is low-substituted methylcellulose.

3. A capsule according to claim 1, wherein the low-substituted cellulose ether is low-substituted hydroxyethylcellulose having a substitution degree of 0.1 to 0.5 for a hydroxyethoxyl group.

4. A capsule according to claim 1, wherein the low-substituted cellulose ether is low-substituted hydroxypropylcellulose having a substitution degree of 0.1 to 0.5 for a hydroxypropoxyl group.

5. A capsule according to claim 1, wherein the low-substituted cellulose ether is low-substituted hydroxypropylmethylcellulose having a substitution degree of 0.1 to 0.5 for a methoxyl group and a substitution degree of 0.1 to 0.5 for a hydroxypropoxyl group.

6. A capsule comprising a shell consisting of (i) low-substituted cellulose ether having a substitution degree of 0.1 to 0.8 which is insoluble in water but soluble in an aqueous alkaline solution and (ii) a plasticizer, wherein said capsule is a hard capsule into which an active ingredient is filled.

7. A capsule according to claim 6, wherein the low-substituted cellulose ether is low-substituted methylcellulose.

8. A capsule according to claim 6, wherein the low-substituted cellulose ether is low-substituted hydroxyethylcellulose having a substitution degree of 0.1 to 0.5 for a hydroxyethoxyl group.

9. A capsule according to claim 6, wherein the low-substituted cellulose ether is low-substituted hydroxypropylcellulose having a substitution degree of 0.1 to 0.5 for a hydroxypropoxyl group.

10. A capsule according to claim 6, wherein the low-substituted cellulose ether is low-substituted hydroxypropylmethylcellulose having a substitution degree of 0.1 to 0.5 for a methoxyl group and a substitution degree of 0.1 to 0.5 for a hydroxypropoxyl group.

11. A capsule according to claim 6, wherein the plasticizer is any one of the following: (i) glycerin or derivative thereof, (ii) propylene glycol or derivative thereof, or (ii) ethylene glycol or derivative thereof.

12. A capsule according to claim 6, wherein the plasticizer is glycerin.

* * * * *